US 6,631,282 B2

(12) United States Patent
Rule et al.

(10) Patent No.: US 6,631,282 B2
(45) Date of Patent: Oct. 7, 2003

(54) DEVICE FOR ISOLATING REGIONS OF LIVING TISSUE

(75) Inventors: Peter Rule, Los Altos Hills, CA (US); James R. Braig, Piedmont, CA (US); Daniel S. Goldberger, Boulder, CO (US); Julian Cortella, Alameda, CA (US); Mark D. Agostino, Alameda, CA (US)

(73) Assignee: OptiScan Biomedical Corporation, Alameda, CA (US)

( * ) Notice: Subject to any disclaimer, the term of this patent is extended or adjusted under 35 U.S.C. 154(b) by 0 days.

(21) Appl. No.: 09/970,021

(22) Filed: Oct. 2, 2001

(65) Prior Publication Data

US 2003/0032872 A1 Feb. 13, 2003

Related U.S. Application Data

(60) Provisional application No. 60/311,521, filed on Aug. 9, 2001.

(51) Int. Cl.[7] .................................................. A61B 5/00
(52) U.S. Cl. ...................................................... 600/344
(58) Field of Search ................................ 600/310, 322, 600/323, 340, 344

(56) References Cited

U.S. PATENT DOCUMENTS

| | | | |
|---|---|---|---|
| 4,798,955 A | * | 1/1989 | Rosenthal ................... 600/310 |
| 4,953,552 A | | 9/1990 | DeMarzo |
| 5,028,787 A | * | 7/1991 | Rosenthal et al. ......... 250/341.5 |
| 5,035,243 A | | 7/1991 | Muz |
| 5,140,985 A | | 8/1992 | Schroeder et al. |
| 5,211,160 A | | 5/1993 | Talish et al. |
| 5,313,941 A | | 5/1994 | Braig et al. |
| 5,419,321 A | | 5/1995 | Evans |
| 5,515,847 A | | 5/1996 | Braig et al. |
| 5,615,672 A | | 4/1997 | Braig et al. |
| 5,642,733 A | | 7/1997 | Archibald et al. |
| 5,769,076 A | | 6/1998 | Maekawa et al. |
| 5,771,890 A | | 6/1998 | Tamada |
| 5,772,587 A | | 6/1998 | Gratton et al. |
| 5,823,951 A | | 10/1998 | Messerschmidt |
| 5,827,183 A | | 10/1998 | Kurnik et al. |
| 5,877,500 A | | 3/1999 | Braig et al. |
| 5,879,373 A | * | 3/1999 | Roper et al. ................. 600/344 |
| 5,900,632 A | | 5/1999 | Sterling et al. |
| 5,991,648 A | | 11/1999 | Levin |
| 6,023,629 A | | 2/2000 | Tamada |
| 6,025,597 A | | 2/2000 | Sterling et al. |
| 6,048,323 A | | 4/2000 | Hon |
| 6,049,081 A | | 4/2000 | Sterling et al. |
| 6,072,180 A | | 6/2000 | Kramer et al. |
| 6,073,038 A | | 6/2000 | Wang et al. |
| 6,161,028 A | | 12/2000 | Braig et al. |
| 6,192,261 B1 | | 2/2001 | Gratton et al. |
| 6,198,949 B1 | | 3/2001 | Braig et al. |
| 6,240,306 B1 | | 5/2001 | Rohrscheib et al. |
| 6,241,663 B1 | | 6/2001 | Wu et al. |
| 6,264,622 B1 | | 7/2001 | Augustine |

FOREIGN PATENT DOCUMENTS

WO      WO 01/30236      5/2001

* cited by examiner

*Primary Examiner*—Eric F. Winakur
(74) *Attorney, Agent, or Firm*—Knobbe Martens Olson & Bear

(57) ABSTRACT

A device and method are provided for use with a non-invasive optical measurement system, such as a thermal gradient spectrometer for improved determination of analyte concentrations within living tissue. In a preferred embodiment, a site selector is secured to a patient's forearm thereby isolating a measurement site on the patient's skin for determination of blood glucose levels. The site selector attaches to a thermal mass window of the spectrometer and thus forms an interface between the patient's skin and the thermal mass window. When the spectrometer must be temporarily removed from the patient's skin, such as to allow the patient mobility, the site selector is left secured to the forearm so as to maintain a consistent measurement site on the skin. When the spectrometer is later reattached to the patient, the site selector will again form an interface between the gradient spectrometer and the same location of skin as before.

22 Claims, 7 Drawing Sheets

DEVICE FOR ISOLATING REGIONS OF LIVING TISSUE

RELATED APPLICATIONS

This application claims priority to U.S. Provisional Patent Application No. 60/311,521, filed Aug. 9, 2001, entitled DEVICE FOR ISOLATING REGIONS OF LIVING TISSUE, the entire contents of which are hereby incorporated by reference.

BACKGROUND OF THE INVENTION

1. Field of the Invention

This invention relates generally to determining analyte concentrations within living tissue. More particularly, this invention relates to a device for isolating regions of living tissue for consistent transfer of thermal spectra to and from the tissue.

2. Description of the Related Art

Millions of diabetics are forced to draw blood on a daily basis to determine their blood glucose levels. A search for a non-invasive methodology to accurately determine blood glucose levels has been substantially expanded in order to alleviate the discomfort of these individuals. A significant advance in the state of the art of non-invasive blood glucose analysis has been realized by an apparatus taught in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001, and by methodology taught in U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000, both of which are hereby incorporated in their entirety by reference.

U.S. Pat. No. 6,198,949 discloses a spectrometer for non-invasive transfer of thermal gradient spectra to and from living tissue. The spectrometer includes an infrared transmissive thermal mass, referred to as a thermal mass window, for inducing a transient temperature gradient in the tissue by means of conductive heat transfer with the tissue, and a cooling system in operative combination with the thermal mass for the cooling thereof. Also provided is an infrared sensor for detecting infrared emissions from the tissue as the transient temperature gradient progresses into the tissue, and for providing output signals proportional to the detected infrared emissions. A data capture system is provided for sampling the output signals received from the infrared sensor as the transient temperature gradient progresses into to the tissue. The transient thermal gradients arising due to the intermittent heating and cooling of the patient's skin generate thermal spectra which yield very good measurements of the patient's blood glucose levels.

Although the apparatus taught in the above-mentioned U.S. Pat. No. 6,198,949 has led to a significant advance in the state of the art of non-invasive blood glucose analysis, one possible source of error arises due to the nature of the contact between the thermal mass window and the patient's skin. If several separate measurements are required, it follows that the thermal mass window must be brought into contact with the patient's skin several times. The problem with this is that each of such contacts tends to be slightly different. For instance, slight differences in skin topology and/or pressure may arise at the interface between the thermal mass window and the skin; the patient may move that portion of his or her body, for instance the arm, which is in contact with the thermal mass window; and muscular tension may change between measurements. Each of these factors, and perhaps others as well, tend to complicate the already complex nature of the contact between the skin and the thermal mass window.

SUMMARY OF THE INVENTION

A device and method are provided for use with a non-invasive optical measurement system, such as but not limited to a thermal gradient spectrometer for improved determination of analyte concentrations within living tissue. In a preferred embodiment, a site selector is secured to a patient's forearm thereby isolating a measurement site on the patient's skin for determination of blood glucose levels. The site selector attaches to or engages a window of the gradient spectrometer and thus forms an interface between the patient's skin and the window. When the spectrometer must be temporarily removed from contact with the patient's skin, such as to allow the patient mobility, the site selector is left secured to the forearm so as to maintain a consistent measurement site on the skin. When the spectrometer is later reattached to the patient, the site selector will again form an interface between the spectrometer and the same location of skin as before.

In one embodiment, a device for use with a non-invasive optical measurement system comprises a generally flat member having an aperture passing from a first surface of the flat member to a second surface of the flat member. The flat member is preferably made of injection-molded plastic, and may be configured to minimize the formation of condensation thereon. The aperture has a predetermined cross-sectional shape and allows substantially unimpeded transmission of thermal spectra to and from skin of a patient through the flat member. The first surface comprises a contact surface which presses against the skin of the patient when the flat member is attached thereto. The second surface comprises an interface surface which is shaped to receive the non-invasive optical measurement system.

A fastening strap may be connected to the flat member and adapted to attach the flat member to a predetermined location on the patient, such as a forearm. The fastening strap comprises a fixed end and an adjustable end. The fixed end passes through a first of opening within the flat member and the adjustable end passes through a second of opening within the flat member such that the fastening strap assumes an annular configuration having an interior surface and an exterior surface. The fixed end is folded back and affixed to the interior surface of the fastening strap, and the adjustable end is folded over and removably attached to the exterior surface of the fastening strap with a fastener such as a buckle or Velcro™.

In another embodiment, the contact surface of the flat member includes adhesive material which is adapted to attach the flat member to the predetermined location on the patient. With this embodiment, the contact surface includes a pressure sensitive adhesive surface which enables attaching the site selector to the patient's skin without using the above-mentioned fastening strap.

In operation the flat member and the aperture cooperate to grip the skin of the patient when pressed against the skin under force applied by the fastening strap. Furthermore, the flat member is coupled with the non-invasive optical measurement system such that removal of the measurement system from the flat member leaves the predetermined location on the patient substantially unaltered.

One aspect of the invention provides a device for maintaining a predetermined location on the skin of a patient to facilitate use of a noninvasive optical measurement system. The device comprises a generally flat member having an aperture passing from a first surface of the flat member to a second surface of the flat member. Preferably, the flat member is made of a rigid material, such as injection-molded plastic. The aperture is adapted to allow substantially unimpeded transmission of thermal spectra to and from skin of a patient through the flat member. The first surface comprises a contact surface which presses against the skin of the patient when the flat member is attached thereto. The second surface comprises an interface surface which is shaped to receive the noninvasive optical measurement system. The interface surface preferably comprises at least one raised section which facilitates orienting the noninvasive optical measurement system relative to the flat member such that the noninvasive optical measurement system assumes angular and axial alignment with the aperture. The aperture preferably comprises at least one protrusion which facilitates attaching the noninvasive optical measurement system to the flat member such that the interface surface receives the noninvasive optical measurement system. The flat member and the aperture cooperate to grip the skin of the patient when applied to the skin.

A fastening strap is connected to the flat member and is adapted to attach the flat member to the predetermined location on the skin of the patient. The fastening strap comprises a fixed end and an adjustable end. The fixed end passes through a first opening within the flat member and the adjustable end passes through a second opening within the flat member such that the fastening strap assumes an annular configuration having an interior surface and an exterior surface. The fixed end is folded back and affixed to the interior surface of the fastening strap, and the adjustable end is folded over and removably attached to the exterior surface of the fastening strap.

Another aspect of the invention provides a method for consistently isolating regions of living tissue for transfer of thermal spectra between the tissue and a noninvasive optical measurement system. The method comprises attaching a site selector to a predetermined region of skin on a patient. The site selector comprises a generally flat member having an aperture passing from a first surface to a second surface of the flat member. The first surface comprises a contact surface which presses against the skin of the patient when the flat member is attached thereto, and the second surface comprises an interface surface which is adapted to receive the noninvasive optical measurement system. The aperture is adapted to allow substantially unimpeded transmission of thermal spectra through the flat member between the contact surface and the interface surface. Pressure between the site selector and the patient's skin causes the perimeter of the aperture to enter into a gripping relationship with the skin, thereby minimizing relative motion between the site selector and the skin. This gripping relationship provides location stability whereby the site selector is prevented from sliding across the skin when the site selector is pushed or otherwise acted on by an external force.

The method further comprises placing the noninvasive optical measurement system in intimate contact with the interface surface of the site selector. A window of the noninvasive optical measurement system interfaces with the aperture and is placed in thermal contact with the predetermined region of skin on the patient. The noninvasive optical measurement system is removably attachable to the site selector such that the noninvasive optical measurement system may be attached to and detached from the site selector while the site selector remains attached to the skin of the patient such that a consistent measurement site on the skin is maintained.

Another aspect of the invention provides a device for consistent placement of a predetermined region of a patient's skin against an analysis window of a noninvasive optical measurement system. The device comprises a contact surface of the noninvasive optical measurement system, which comprises the analysis window, a first alignment window, and a second alignment window, a first alignment mark printed on the patient, and a second alignment mark printed on the patient. Alignment of the first and second alignment windows respectively with the first and second alignment marks causes the predetermined region to align with the analysis window. Preferably, the first and second alignment windows each provides optical access to skin of the patient, and thus enables visual navigation of the noninvasive optical measurement system on the skin.

Still another aspect of the invention provides a method of consistently isolating regions of living tissue for transfer of thermal spectra between the tissue and a noninvasive optical measurement system. The method comprises applying a first alignment mark and a second alignment mark to a region of skin on a patient such that when the first alignment mark is coincident with a first alignment detector of the noninvasive optical measurement system and the second alignment mark is coincident with a second alignment detector of the noninvasive optical measurement system, an analysis window of the noninvasive optical measurement system is caused to be centered and aligned with a predetermined location on the skin. The method further comprises placing the window of the noninvasive optical measurement system in thermal contact with the predetermined location on the skin, and moving the skin and/or the noninvasive optical measurement system relatively until the first and second alignment detectors are centered and aligned respectively with the first and second alignment marks.

In another aspect of the invention, a device is provided for consistently isolating regions of living tissue for transfer of thermal spectra between the tissue and a noninvasive optical measurement system. The device comprises a site selector comprising a generally flat member having an aperture passing from a first surface of the flat member to a second surface of the flat member. Preferably, the flat member is made of injection-molded plastic comprising a material which minimizes a formation of condensation thereon. The aperture is adapted to allow substantially unimpeded transfer of thermal spectra through the flat member. The first surface comprises a contact surface which presses against the skin of the patient when the flat member is attached thereto. The aperture grips the skin of the patient when the site selector is pressed thereon such that relative motion between the site selector and the skin is minimized. The second surface comprises an interface surface which is shaped to receive the noninvasive optical measurement system.

The device further comprises an alignment marker printed onto the skin of the patient. Aligning the aperture with the alignment mark facilitates orienting the site selector relative to a predetermined location on the patient such that when the noninvasive optical measurement system is coupled with the site selector, the noninvasive optical measurement system is centered and aligned with the predetermined location on the patient.

In still another aspect of the invention, a method is provided for consistently positioning a predetermined region of a patient's skin against a window of a noninvasive optical measurement system. The method comprises applying an alignment mark to the skin of the patient, aligning a site selection member with the alignment mark and securing the site selection member with respect to the skin of the patient, and coupling the noninvasive optical measurement system to the site selection member, thereby bringing the window of the noninvasive optical measurement system into thermal contact with the predetermined region on the patient. The site selection member preferably comprises a flat member having an aperture passing from a first surface of the flat member to a second surface of the flat member. The aperture allows substantially unimpeded transmission of thermal spectra to and from the skin of the patient through the flat member. The first surface comprises a contact surface which presses against the skin of the patient when the flat member is attached thereto, and the second surface comprises an interface surface which is shaped to receive the noninvasive optical measurement system.

DETAILED DESCRIPTION OF THE PREFERRED EMBODIMENT

The preferred embodiments of the present invention described below relate particularly to a site selector for consistent transfer of thermal spectra to and from living tissue. While the description sets forth various embodiments and specific details, it will be appreciated that the description is illustrative only and should not to be construed in any way as limiting the invention. Furthermore, various applications of the invention, and modifications thereof, which may occur to those skilled in the art, are also encompassed by the general concepts described below.

Figure 1:
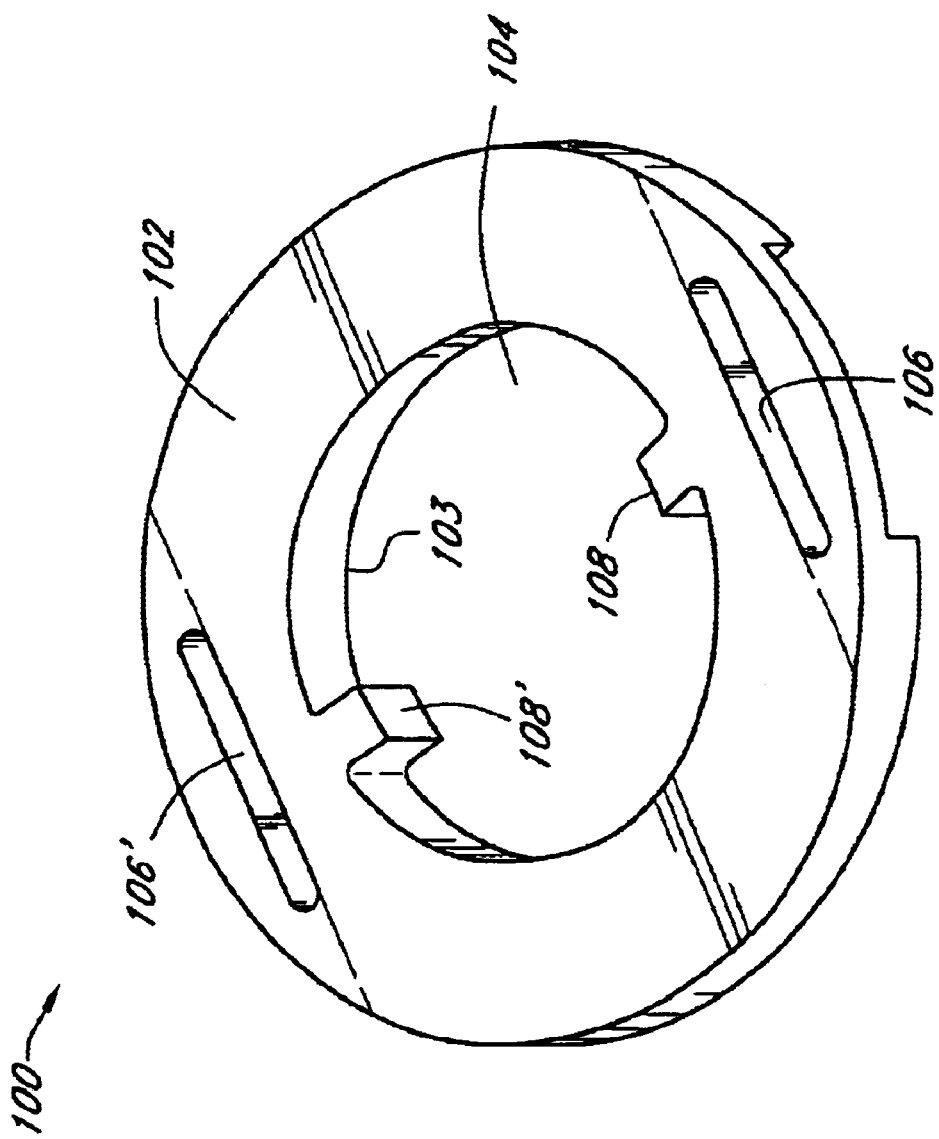
FIG. 1 is a perspective view of one embodiment of a site selector.

FIG. 1 is a perspective view of one embodiment of a site selector 100. It is contemplated that the site selector 100 is to be used in conjunction with a non-invasive optical measurement system such as, but not necessarily limited to, the apparatus taught in the above-mentioned U.S. Pat. No. 6,198,949. This patent teaches that the non-invasive thermal gradient spectrometer comprises a window and a thermal mass window, wherein the window forms an interface between the thermal mass window and a patient's skin. It is contemplated that the site selector 100 couples with, or otherwise operates in conjunction with the window and thus stabilizes the interface between the window and the patient's skin. It is further contemplated that the site selector 100 may be used in conjunction with the noninvasive thermal gradient spectrometer in accordance with the methodology taught in the above-mentioned U.S. Pat. No. 6,161,028.

Figure 3:
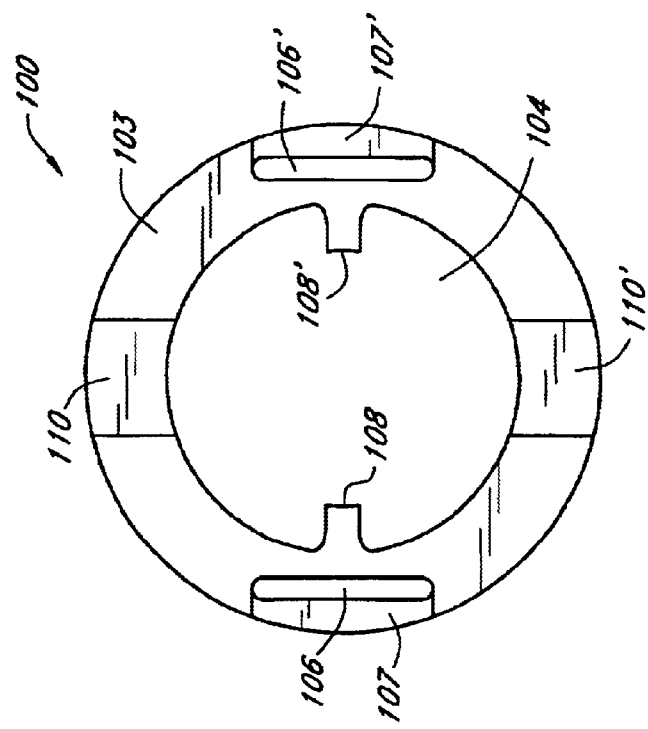
FIG. 3 is a top view of the site selector of FIG. 2, taken along line 3—3.
Figure 2:
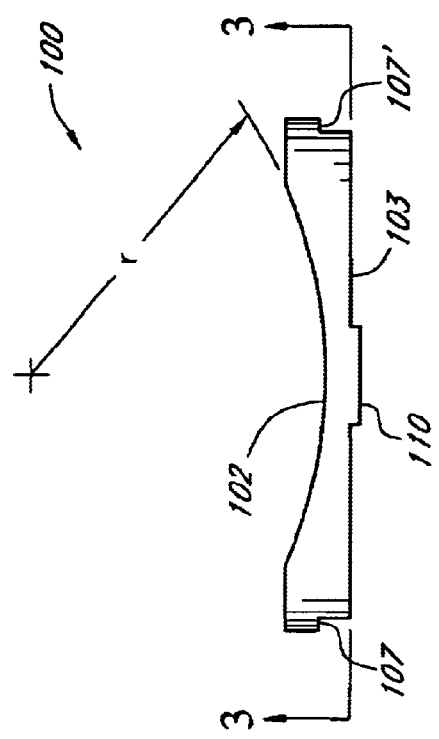
FIG. 2 is a side elevation view of the site selector of FIG. 1.

In the embodiment illustrated in FIG. 1, the site selector 100 is a generally flattened, rigid member comprising a contact surface 102, an interface surface 103, an aperture 104, openings 106, 106', and protrusions 108, 108'. As illustrated in FIGS. 2 and 3, the site selector 100 further comprises channels 107, 107', and raised sections 110, 110'. The openings 106, 106' and the channels 107, 107' facilitate fastening the site selector 100 to a patient (see FIG. 5). The site selector 100 may be formed of injection-molded plastic or other similar material such that a non-invasive optical measurement system, such as the thermal gradient spectrometer taught in U.S. Pat. No. 6,198,949, may be coupled with the site selector 100 with minimal movement arising therebetween. Furthermore, it is contemplated that the material comprising the site selector 100 may be such that condensation formed thereon when the site selector 100 is exposed to cooler temperatures (below the dew point) is substantially minimized.

The contact surface 102 presses against the patient's skin when the site selector 100 is strapped thereon or otherwise secured thereto. As can be seen most clearly in FIG. 2, the contact surface 102 comprises a radius of curvature r which conforms to the topology of the location on the patient's body where the site selector 100 is intended to be used. In a preferred embodiment, wherein the site selector 100 is intended for use on a forearm 150, the contact surface 102 is curved and has a radius of curvature r of about 3.0 inches. It will be apparent to those skilled in the art that, depending upon where on a patient the site selector 100 is intended to be used, the contact surface 102 may advantageously be formed with other shapes or other radii of curvature r without departing from the scope of the invention.

The interface surface 103 receives or otherwise engages with the above-mentioned non-invasive optical measurement system. The protrusions 108, 108' and the raised sections 110, 110' respectively facilitate attaching and/or aligning the optical measurement system to the site selector 100. As will be appreciated by those of ordinary skill in the art, the configuration of the interface surface 103 (which, in the illustrated embodiment, includes the specific number, shapes, orientations, and characteristics of the protrusions 108, 108' and the raised sections 110, 110') is dependent upon the particular type of instrument with which the site selector 100 is intended to be used. On this basis, the number, shapes, orientations and characteristics of the protrusions 108, 108' and the raised sections 110, 110' (or the choice of structure used in place of or in addition to the protrusions 108, 108' and the raised sections 110, 110') may be substantially altered without departing from the scope of the invention.

Referring to FIGS. 1 and 3, the aperture 104 allows substantially unimpeded transmission of thermal spectra to and from the patient's skin through the site selector 100. The aperture 104 preferably has a substantially circular cross-section having a diameter of about 2.0 inches. It will be appreciated, however, that while in the embodiment of FIGS. 1 and 3 the aperture 104 has a circular cross-sectional shape, other cross-sectional shapes and sizes are contemplated, such as, by way of example, rectangular, circular, diamond, elliptical, and ovoid. It will further be appreciated that different cross-sectional shapes and sizes may advantageously be combined, thereby forming additional cross-sectional shapes without departing from the scope of the invention.

Alternatively, the aperture 104 may comprise a substrate which serves as a thermal window. The substrate preferably is made of a material having a high thermal conductivity, such as polycrystalline float zone silicon or other similar material, such that the substrate is transparent to thermal spectra. In addition, the substrate may have a thickness sized such that thermal spectra are substantially unimpeded in passing through the substrate. It is contemplated that a suitable substrate which may be used with the site selector 100 of FIGS. 1 through 3 has a thickness of about 0.25 millimeters. It is further contemplated that the substrate has a cross-sectional shape and size such that the substrate is receivable by the aperture 104, thereby facilitating fastening of the substrate to the site selector 100. In one embodiment, the substrate may be permanently affixed within the aperture 104. In another embodiment, the substrate 104 may be removably inserted into the aperture 104. In the latter embodiment, the substrate may further comprise a disposable member which is attachable to and detachable from the site selector 100. It will be appreciated by those of ordinary skill in the art, however, that the substrate may be comprised of other materials, cross-sectional shapes and thicknesses without detracting from the scope of the invention.

As a further alternative, a heating element may be disposed upon the above-mentioned substrate such that the heating element can heat the substrate and the skin when the site selector 100 is strapped to the patient. The heating element transfers heat to the skin of the patient, and thus gives rise to the heating component of the aforementioned intermittent heating and cooling of the patient's skin. One embodiment of the heating element comprises an adhesion layer of gold or platinum (hereinafter referred to as the "gold" layer) deposited over an alloy layer which is applied to the substrate. The alloy layer comprises a material suitable for implementation of the heating element, such as, by way of example, 10/90 titanium/tungsten, titanium/platinum, nickel/chromium, or other similar alloy. The gold layer preferably has a thickness of 4000 Å, and the alloy layer preferably has a thickness ranging between 300 Å and 500 Å. The gold layer and/or the alloy layer may be deposited onto the substrate 104 by chemical deposition including, but not necessarily limited to, vapor deposition, liquid deposition, plating, laminating, casting, sintering, or other forming or deposition methodologies well known to those of ordinary skill in the art. Once the gold and alloy layers have been deposited onto the substrate, the heating element may be created by etching or removing material from the gold and alloy layers such that a grid structure is formed, as is discussed in the above-mentioned U.S. Pat. No. 6,198,949.

It will be apparent to those of ordinary skill in the art that the heating element may comprise a grid structure which is formed as the material is being deposited onto the surface of the substrate by use of a mask or other known techniques. It is contemplated that such a heating element comprises materials, dimensions, and thermal properties which are substantially the same as those mentioned above.

In an alternative embodiment, the site selector 100 may be made of a flexible, semi-compliant material which allows the site selector 100 to be bent such that it conforms to various regions of a patient's body. In one embodiment, the site selector 100 may be made of polyurethane. In another embodiment, the site selector 100 may be made of polypropylene. In still another embodiment, the site selector 100 may be made of silicone. Other embodiments may include other non-compliant or semi-compliant materials, or blends thereof, including but not limited to EVA (Ethylene-Vinyl-Acetate), PVC, PET, and NYLON. Those of ordinary skill in the art will recognize that the site selector 100 may advantageously be made of other non-compliant or semi-compliant, biocompatible materials without departing from the scope of the invention.

Figure 4:
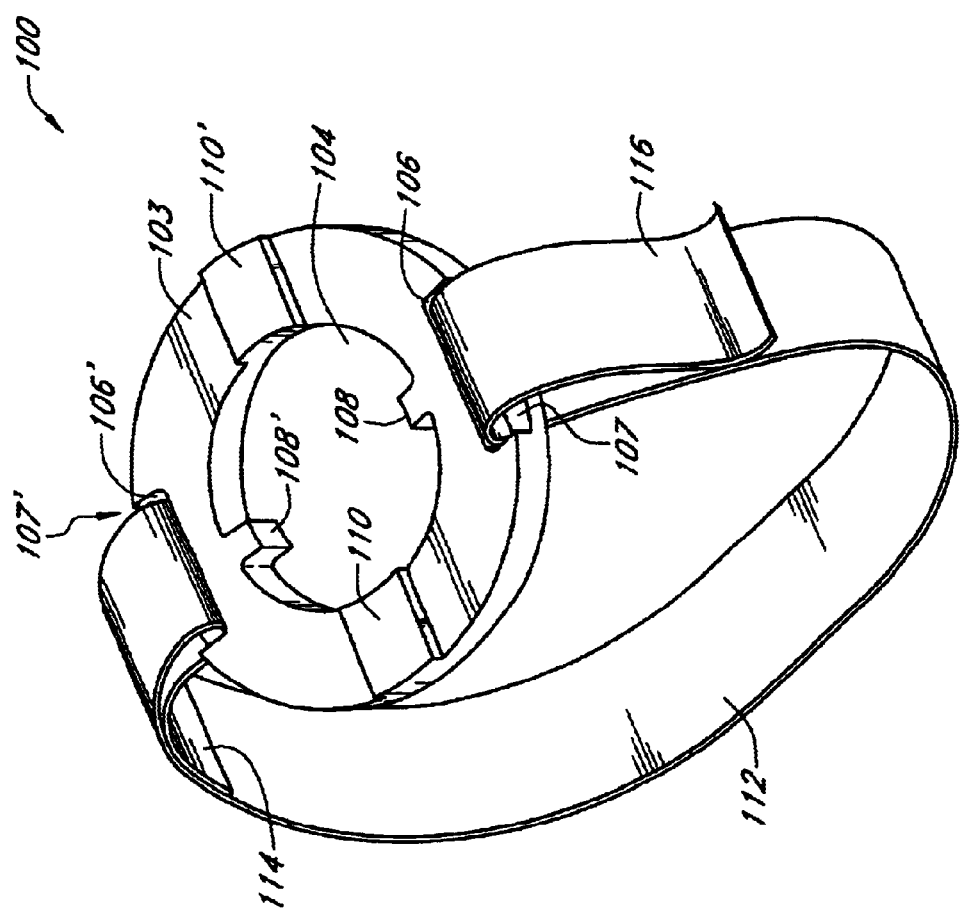
FIG. 4 is a perspective view of the site selector of FIG. 1 with an attached fastening strap.

FIG. 4 is a perspective view illustrating the site selector 100 with one embodiment of a fastening strap 112 that may be used in conjunction with the site selector 100. In the illustrated embodiment, the fastening strap 112 comprises a fixed end 114 and an adjustable end 116, which pass through the openings 106', 106, respectively. The channels 107, 107' allow the fixed and adjustable ends 114, 116 to pass into the openings 106, 106' without rising above the plane of the interface surface 102. After passing through the opening 106', the fixed end 114 is folded back and affixed to an interior surface of the strap 112. Similarly, after passing through the opening 106, the adjustable end 116 is folded over and affixed to an exterior surface of the strap 112. The adjustable end 116 is removably attachable to the strap 112, thereby facilitating fastening of the site selector 100 onto the patient (see FIG. 5), as well as subsequent removal therefrom. The fixed and adjustable ends 114, 116 preferably include strips of Velcro™ (not shown) or other similar material which facilitates repeated attaching, adjusting and removing of the fastening strap 112 from the site selector 100.

A person of ordinary skill in the art will recognize that other techniques may advantageously be utilized for placing the site selector 100 in contact with the patient's skin. For example, in another embodiment the contact surface 102 may include an adhesive material which is adapted to attach the site selector 100 to the predetermined location on the patient. With this embodiment, the contact surface 102 comprises a pressure sensitive adhesive surface which enables attaching the site selector 100 to the patient's skin without using the fastening strap 112.

Figure 5:
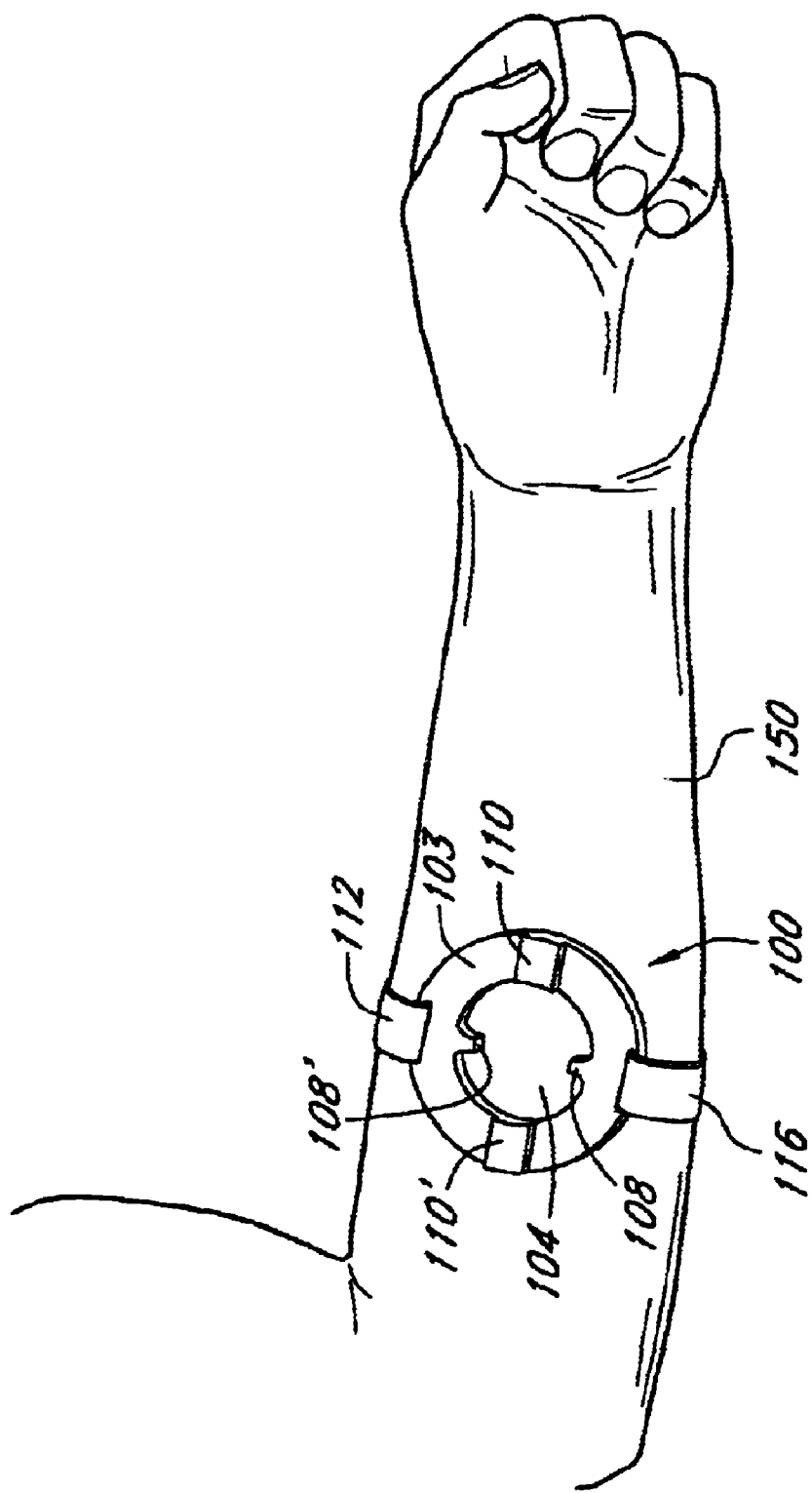
FIG. 5 shows the site selector of FIG. 1 strapped onto a forearm of a patient.

FIG. 5 generally illustrates the use of the site selector 100 on the forearm 150 of the patient. As is illustrated, the site selector 100 is strapped to the forearm 150 such that the contact surface 102 is pressed against the patient's skin, while the interface surface 103, as well as the raised sections 110, 110', face outward away from the skin. Pressure between the site selector 100 and the patient's skin causes the perimeter of the aperture 104 to "grip" the skin, thereby substantially minimizing relative motion between the skin and the site selector 100. This gripping of the skin provides location stability whereby the site selector 100 is prevented from sliding across the patient's skin when pushed or otherwise acted on by external forces, such as forces arising when the non-invasive optical measurement system is attached and detached from the site selector 100.

As will be apparent to those of ordinary skill in the art, the site selector 100 covers up a region of the skin surrounding the portion of skin from which thermal spectral readings are taken, and prevents moisture evaporation from the covered region of skin. This is believed to preserve and stabilize the hydration level within the skin area from which readings are taken, as well as to reduce variance and error observed in repeated measurements over time.

In operation, a non-invasive optical measurement system, such as the apparatus taught in U.S. Pat. No. 6,198,949, is placed in intimate contact with the interface surface 103 such that a window of the measurement system interfaces with the aperture 104 and is placed in thermal contact with the patient's skin. If, for some reason, the measurement system must be temporarily removed from the patient's skin, such as to allow the patient mobility, the site selector 100 may be left strapped to the forearm 150 so as to maintain a consistent measurement site on the skin. When the measurement system is later reattached to the site selector 100, the site selector 100 will again place the window of the measurement system in thermal contact with the same location of skin as before. This substantially reduces measurement errors arising due to the otherwise variable nature of the contact between the measurement system and the patient's skin.

It is to be understood that the site selector 100 is not restricted to use solely with the forearm 150. For example, the site selector 100 may advantageously be attached to the end of an index finger. Still, one site selector 100 may be attached to the index finger while a second somewhat larger site selector 100 is at the same time attached to the forearm 150, thereby allowing for comparison of measured values. It will be appreciated by those of ordinary skill in the art that the site selector 100 may advantageously be placed in intimate contact with any location of skin whereupon satisfactory measurements can be obtained.

Figure 6:
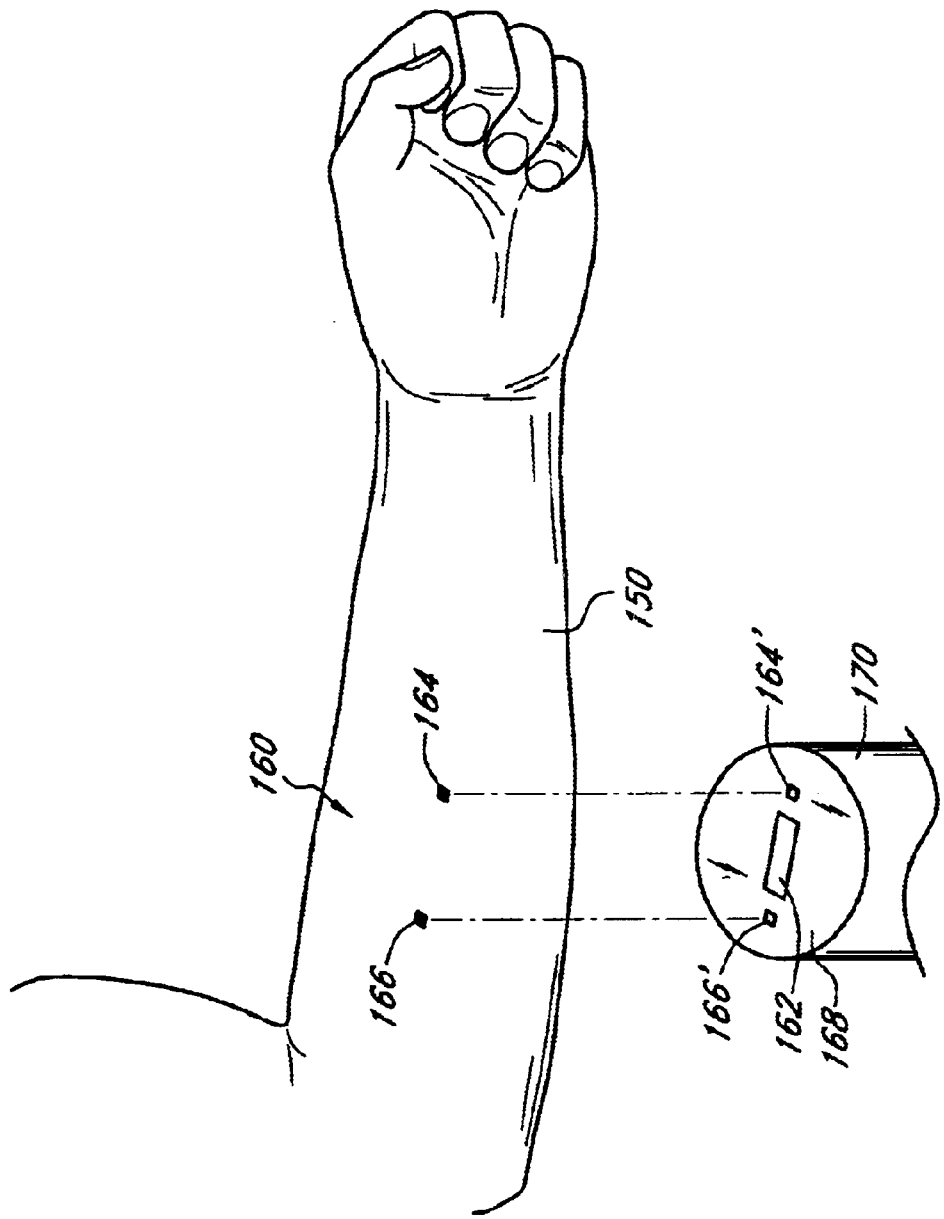
FIG. 6 illustrates another embodiment of a site selector on a forearm of a patient.

FIG. 6 illustrates another embodiment of a site selector 160 which may be used on the forearm 150 of the patient. The site selector 160 comprises a first window alignment mark 164 and a second window alignment mark 166, both of which are printed, drawn or tattooed on the forearm 150. The site selector 160 facilitates the positioning of a window 162 of an optical measurement system 170 on a predetermined location of skin. The window 162 serves to form an interface between a thermal mass window (not shown) within the optical measurement system 170 and the patient's skin. As shown, the first alignment mark 164 corresponds with a first alignment window 164', which comprises a portion of a contact surface 168 of the optical measurement system 170. Similarly, the second alignment mark 166 corresponds with a second alignment window 166', which also comprises a portion of the contact surface 168. The window alignment marks 164, 166 and the alignment windows 164', 166' facilitate orienting the optical measurement system 170 relative to the forearm 150 such that the window 162 is centered and aligned with the predetermined location of the skin. It is contemplated that the alignment windows 164', 166' each provides direct visual or optical access to the skin, thereby enabling a practitioner to visually navigate the optical measurement system 170 on the skin. This may be facilitated by providing the practitioner with an image of the field of view of the windows 164', 166', or by linking the windows 164', 166' to an optical detection system which is tuned to detect alignment of the marks 164, 166 over the windows 164', 166'.

In operation, the alignment marks 164, 166 are applied to the forearm 150 of the patient. A non-invasive optical measurement system 170, such as the apparatus taught in U.S. Pat. No. 6,198,949, is then coupled to the site selector 100 placing the window 162 in thermal contact with the patient's skin. While in contact with the measurement system 170, the patient's skin is moved on the system 170 (or vice versa) until the alignment marks 164, 166 become aligned with the alignment windows 164', 166', respectively. If, for some reason, the measurement system 170 must be temporarily removed from the patient's skin, such as to allow the patient mobility, the site selector 160 remains on the forearm 150 designating a consistent measurement site on the skin. When the measurement system 170 is later attached to the patient, the site selector 160 will again enable placement of the window 162 of the measurement system 170 in contact with the same location of skin as before.

Figure 7:
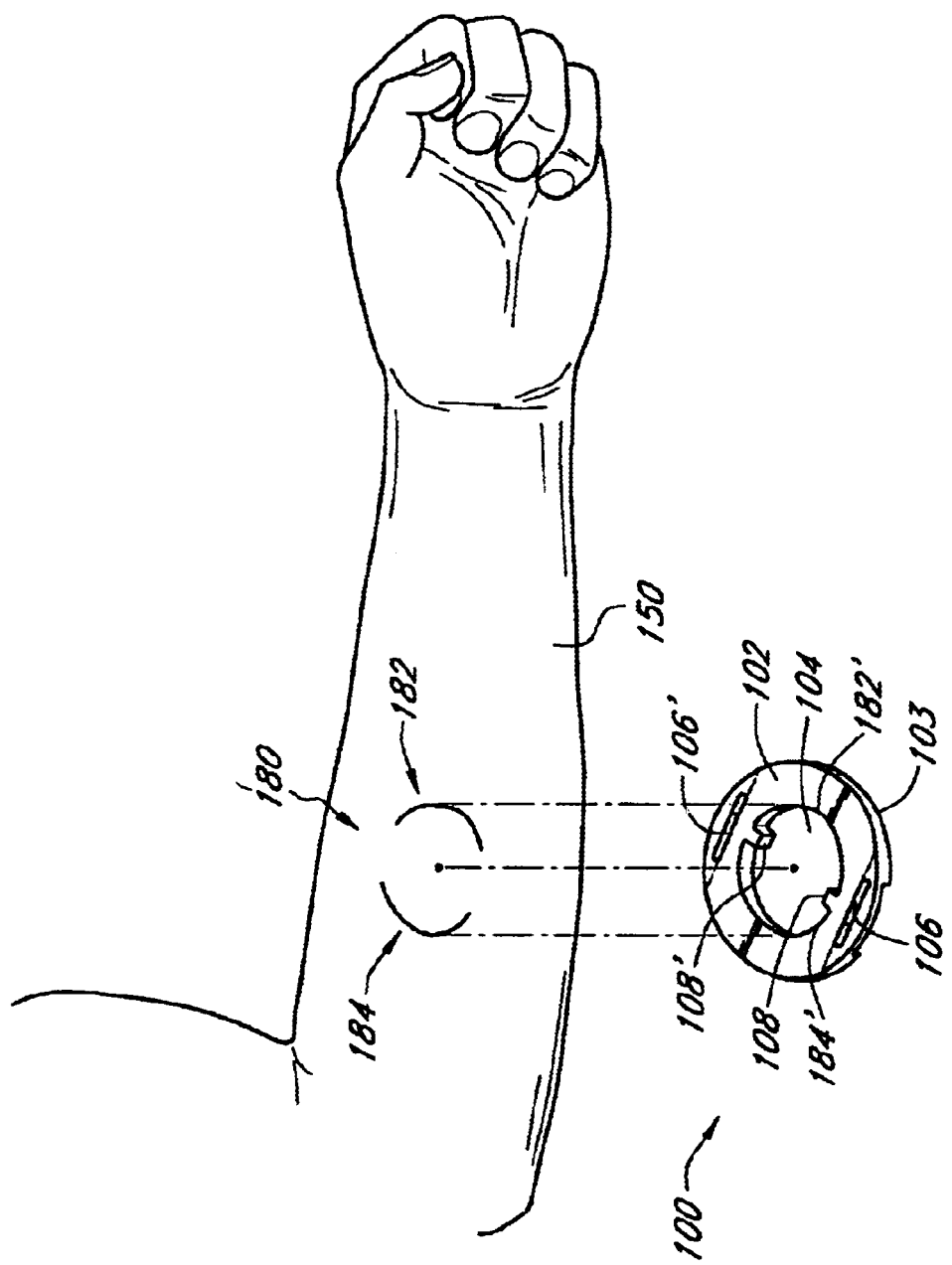
FIG. 7 illustrates one embodiment of an alignment marker which may be used in conjunction with the site selector of FIG. 1 on a forearm of a patient.

FIG. 7 shows one embodiment of an alignment marker 180 which may be used in conjunction with the site selector 100 on the forearm 150 of the patient. The alignment marker 180 preferably comprises a first alignment mark 182 and a second alignment mark (or, where sufficient, a single alignment mark) 184, both of which are printed, drawn or tattooed on the forearm 150. The alignment marker 180 facilitates the positioning of site selector 100 on a predetermined location of skin. As shown, the first alignment mark 182 corresponds with a side 182' of the site selector 100 and the second alignment mark 184 corresponds with an opposing side 184' of the site selector 100. Alternatively, the marks 182, 184 may be placed on the skin such that the marks 182, 184 correspond and align with opposite sides of the outer perimeter of the site selector 100. The alignment marks 182, 184 facilitate orienting the site selector 100 relative to the forearm 150 such that the aperture 104 is centered and aligned with the predetermined location of the skin. It is contemplated that the alignment marks 182, 184 are separated by a distance whereby the marks 182, 184 are out of the field of view of the window 162 (see FIG. 6) when the site selector 100 is properly oriented relative to the marks 182, 184.

In operation, the alignment marks 182, 184 are applied to the forearm 150 of the patient. The site selector 100 is then fastened to the forearm 150 and the patient's skin is moved on the site selector 100 (or vice versa) until the alignment marks 182, 184 become respectively aligned with the sides 182', 184' of the aperture 104. Once the site selector 100 is properly positioned on the forearm 150, the non-invasive optical measurement system 170 (see FIG. 6) is coupled to the interface surface 103 such that the window 162 is placed in thermal contact with the patient's skin. If, for some reason, the measurement system 170 and the site selector 100 must be temporarily removed from the patient's skin, the alignment marks 182, 184 remain on the forearm 150 designating a consistent measurement site on the skin. When the site selector 100 is later reattached to the patient's skin, the alignment marks 182, 184 will again enable placement of the site selector 100 and the measurement system 170 in contact with the same location of skin as before. This substantially reduces measurement errors arising due to the otherwise variable nature of the contact between the measurement system 170 and the patient's skin.

Figure 8:
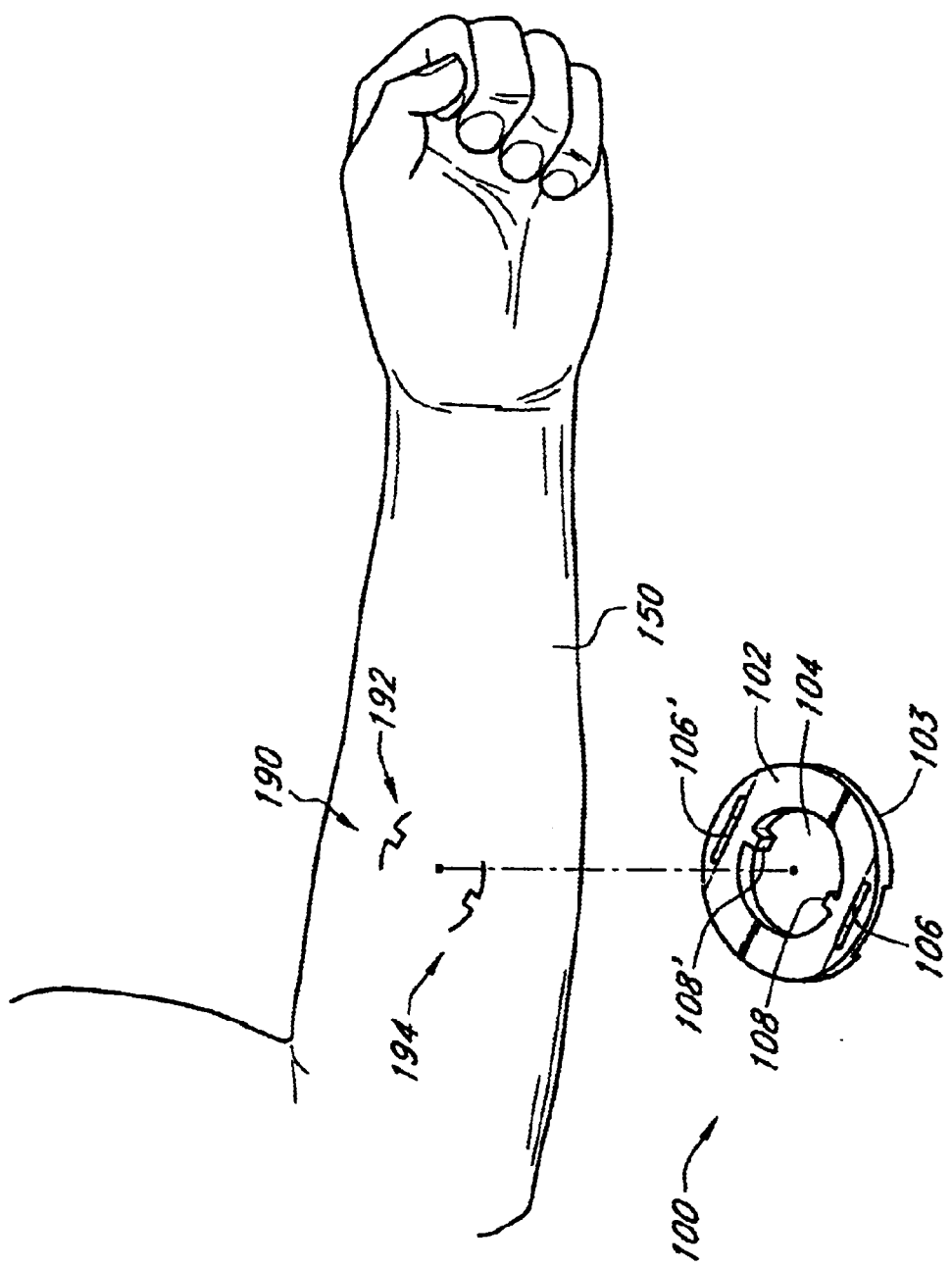
FIG. 8 illustrates another embodiment of an alignment marker which may be used in conjunction with the site selector of FIG. 1 on a forearm of a patient.

FIG. 8 illustrates another embodiment of an alignment marker 190 which may be used in conjunction with the site selector 100. The alignment marker 190 comprises a first alignment mark 192 and a second alignment mark 194 which are both printed, drawn or tattooed on the forearm 150. The alignment marker 190 facilitates the positioning of site selector 100 on a predetermined location of skin. In the embodiment illustrated in FIG. 8, the first alignment mark 192 corresponds with the protrusion 108 of the site selector 100 and the second alignment mark 194 corresponds with the opposing protrusion 108' of the site selector 100. The alignment marks 192, 194 facilitate orienting the site selector 100 relative to the forearm 150 such that the aperture 104 is centered and aligned with the predetermined location of the skin. It is contemplated that the alignment marks 192, 194 are separated by a distance whereby the marks 192, 194 are out of the field of view of the window 162 (see FIG. 6) when the site selector 100 is properly oriented relative thereto.

The function of the alignment marker 190 illustrated in FIG. 8 is substantially similar to the function of the alignment marker 180 illustrated in FIG. 7. The alignment marks 192, 194 are applied to the forearm 150 of the patient and the site selector 100 is fastened to the forearm 150. The patient's skin is then moved on the site selector 100 (or vice versa) until the alignment marks 192, 194 become respectively aligned with the protrusions 108, 108' within the aperture 104. Once the site selector 100 is properly positioned on the forearm 150, the optical measurement system 170 is coupled to the interface surface 103 such that the window 162 is placed in thermal contact with the patient's skin. If the measurement system 170 and the site selector 100 are removed from the patient's skin, the alignment marks 192, 194 remain on the forearm 150 designating a consistent measurement site on the skin. When the site selector 100 is again fastened onto the patient's skin, the alignment marks 192, 194 will facilitate the positioning of the site selector 100, and consequently the measurement system 170, over the same location of skin as before.

It is to be understood that the alignment markers 180, 190 are not restricted to use solely with the forearm 150. For example, the alignment markers 180, 190 may advantageously be printed, drawn or tattooed on the end of an index finger. Still, one of the alignment markers 180, 190 may be applied to the index finger while a second somewhat larger embodiment of the alignment markers 180, 190 is applied to the forearm 150, thereby enabling a use of two site selectors 100 at the same time for a comparison of measured values. It will be appreciated by those of ordinary skill in the art that the alignment markers 180, 190 may advantageously be applied to any location of skin whereupon use of the site selector 100 yields satisfactory measurements. It will be further appreciated that the alignment markers 180, 190 may advantageously be combined to form other types of alignment markers having different shapes, sizes, and orientations.

Although preferred embodiments of the invention have been described in detail, certain variations and modifications will be apparent to those skilled in the art, including embodiments that do not provide all of the features and benefits described herein. Accordingly, the scope of the invention is not to be limited by the illustrations or the foregoing descriptions thereof, but rather solely by reference to the appended claims.

What is claimed is:

1. A device for maintaining a predetermined location and orientation on the skin of a patient to facilitate use of a noninvasive optical measurement system having an analysis window for collecting infrared emissions from the patient, the device comprising:

a generally flat rigid member adapted to be coupled to said predetermined location on the under portion of the forearm of the patient, the rigid member having a first generally flat surface for engagement with the optical measurement system and a second generally arcuate surface adapted to conform generally to and engage with the forearm of the patient;

a perimeter portion of said rigid member defining an aperture for receiving the analysis window of the optical measurement system;

at least one protrusion extending from said perimeter into the aperture and adapted to cooperate with the optical measurement system to locate and align the measurement system;

slots formed in the perimeter portion of the rigid member; and a strap extending through the slots and coupled to the rigid member, the strap having at least one adjustable end and having an adjustable length for causing the perimeter portion of the rigid member to press against the skin of the patient;

wherein the strap and the rigid member cooperate to put pressure on the perimeter portion of the rigid member whereby the perimeter portion grips the skin to ensure thermal contact between the skin and the analysis window through the aperture.

2. The device of claim 1, wherein said aperture is substantially circular and said at least one protrusion comprises a first protrusion and a second protrusion spaced about 180 degrees from said first protrusion.

3. The device of claim 1, wherein said at least one protrusion forms a substantially flat surface that faces toward an inner portion of said aperture.

4. The device of claim 1, further comprising at least one raised section formed on the first surface and configured to align the optical measurement system to the rigid member.

5. The device of claim 4, wherein said at least one raised section comprises a first raised section and a second raised section located on opposite sides of said aperture.

6. The device of claim 1, wherein said rigid member is formed from a material which minimizes formation of condensation on said rigid member.

7. The device of claim 1, wherein said aperture is substantially circular and has a diameter of about 2.0 inches.

8. A device for maintaining a predetermined location and orientation on the skin of a patient to facilitate use of a noninvasive optical measurement system having an analysis window for collecting infrared emissions from the patient, the device comprising:

a generally flat rigid member adapted to be coupled to said predetermined location on the under portion of the forearm of the patient, the rigid member having a first surface configured for engagement with the optical measurement system and a second generally arcuate surface adapted to conform generally to and engage with the forearm of the patient;

an aperture formed in said rigid member for receiving the analysis window of the optical measurement system;

at least one protrusion formed on said rigid member and extending into the aperture and adapted to cooperate with the optical measurement system to locate and align the measurement system; and a strap coupled to the rigid member, the strap being configured to compress the rigid member against the predetermined location causing the edges of the aperture to press against the skin of the patient, whereby the rigid member grips the skin to ensure thermal contact between the skin and the analysis window through the aperture.

9. The device of claim 8, wherein said aperture is substantially circular and said at least one protrusion comprises a first protrusion and a second protrusion spaced about 180 degrees from said first protrusion.

10. The device of claim 8, wherein said at least one protrusion forms a substantially flat surface that faces toward an inner portion of said aperture.

11. The device of claim 8, further comprising at least one raised section formed on the first surface and configured to align the optical measurement system to the rigid member.

12. The device of claim 11, wherein said at least one raised section comprises a first raised section and a second raised section located on opposite sides of said aperture.

13. The device of claim 8, wherein said rigid member is formed from a material which minimizes formation of condensation on said rigid member.

14. The device of claim 8, wherein said aperture is substantially circular and has a diameter of about 2.0 inches.

15. A method of maintaining a predetermined location on the skin at the under portion of the forearm of a patient to facilitate use of a noninvasive optical measurement system having an analysis window for collecting infrared emissions from the patient, the method comprising:

compressing against the predetermined location a generally flat rigid member having a first generally flat surface configured for engagement with the optical measurement system and a second generally arcuate surface adapted to conform generally to the predetermined location;

causing edges of an aperture formed in the rigid member to press against the skin of the patient; and while the rigid member is compressed against the predetermined location, placing the noninvasive optical measurement system against the first surface of the rigid member and aligning the measurement system by employing a protrusion that is formed on the rigid member and extends into the aperture.

16. The method of claim 15, wherein compressing comprises adjusting the length of a strap coupled to said rigid member.

17. The method of claim 15, wherein aligning comprises employing first and second protrusions located on opposite sides of said aperture.

18. The method of claim 15, wherein aligning further comprises employing a raised portion located on said first surface.

19. The method of claim 15, wherein aligning further comprises employing a first and second raised portion located on said first surface, on opposite sides of said aperture.

20. The method of claim 15, further comprising applying at least one alignment mark to said predetermined location.

21. The method of claim 20, further comprising aligning said rigid member with said at least one alignment mark.

22. The method of claim 20, wherein said alignment mark comprises a first alignment mark and a second alignment mark, the first alignment mark corresponding with a first side of the aperture and the second alignment mark corresponding with a second side of the aperture.

\* \* \* \* \*